US006613742B1

(12) United States Patent
Huang et al.

(10) Patent No.: US 6,613,742 B1
(45) Date of Patent: Sep. 2, 2003

(54) CHEMOKINE-DERIVED SYNTHETIC PEPTIDES

(75) Inventors: Ziwei Huang, Philadelphia, PA (US); Zhaowen Luo, Philadelphia, PA (US); Naiming Zhou, Bala Cynwyd, PA (US); Jiansong Luo, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 0 days.

(21) Appl. No.: 09/543,940

(22) Filed: Apr. 6, 2000

Related U.S. Application Data

(60) Provisional application No. 60/128,106, filed on Apr. 7, 1999.

(51) Int. Cl.⁷ .............................................. A61K 38/00
(52) U.S. Cl. ..................... 514/12; 424/85.1; 435/69.1; 530/300; 530/324; 530/333; 530/351
(58) Field of Search ..................... 424/85.1; 435/69.1; 530/300, 350, 351, 324, 333; 514/12

(56) References Cited

FOREIGN PATENT DOCUMENTS

WO       WO 99/11655       3/1999

OTHER PUBLICATIONS

Luo et al. The role of poitively charged residues in CXCR4 recognition probed with synthetic peptides. Biochemical and Biophysical Research Communications (1999) vol. 263, 691–695.*
Heveker et al. Dissociation of the signalling and antiviral properties of SDF–1 derived small peptides. Current Biology (1998) vol. 8, pp. 369–376.*
Sergel et al. A single amino acid change in Newcastel disease virus fusion protein alters the requirements for HN protein in fusion. Journal of Virology (2000) vol. 74, pp. 5101–5107.*
Abaza et al. Effects of amino acid substitutions outside antigenic site on a protein binding to monoclonal antibodies . . . Journal of Protein Chemistry (1992) vol. 11, pp. 433.*
Ngo et al., Computational complexity, protein structure prediction and the Levinthal paradox. In: The Protein Folding Problem and Tertiary Structure Prediction, Mertz et al. Ed. (1994) pp. 491–495.*
Tashiro et al., "Signal sequence trap: a cloning strategy for secreted proteins and type I membrane proteins", *Science*, 261: 600–603 (1993).
Shirozu et al., "Structure and chromosomal localization of the human stromal cell–derived factor 1 (SDF1) gene", *Genomics*, 28: 495–500 (1995).
Murphy, P.M., "The Molecular Biology of leukocyte chemoattractant receptors", *Annu. Rev. Immunol.*, 12:593–633 (1994).

Premack, B.A., and Schall, T.J., "Chemokine receptors: gateways to inflammation and infection", *Nature Medicine*, 2:1174–8 (1996).
Bandres et al., "Human immunodeficiency virus (HIV) envelope binds to CXCR4 independently of CD4, and binding can be enhanced by interaction with soluble CD4 or by HIV envelope deglycoslation", *Journal of Virology*, 72:2500–2504 (1998).
Bleul et al., "The lymphocyte chemoattractant SDF–1 is a ligand for LESTR/fusin and blocks HIV–1 entry", *Nature*, 382:829–833 (1996).
Oberlin et al., "The CXC chemokine SDF–1 is the ligand for LESTR/fusin and prevents infection by T–cell–line–adapted HIV–1", *Nature*, 383:833–835 (1996).
Murakami et al., "A small molecule CXCR4 inhibitor that blocks T cell line–tropic HIV–1 infection", *J. Exp. Med.*, 186:1389–1393 (1997).
Schols et al., "Inhibition of T–tropic HIV strains by selective antagonization of the chemokine receptor CXCR4", J. Exp. Med., 186:1383–1388 (1997).
Donzella et al., "AMD3100, a small molecule inhibitor of HIV–1 entry via the CXCR4 co–receptor", *Nature Medicine*, 4:72–77 (1998).
Doranz et al., "A small–molecule inhibitor directed against the chemokine receptor CXCR4 prevents it use as an HIV–1 coreceptor", *J. Exp. Med.*, 186:1395–1400 (1997).
Heveker et al., "J. Dissociation of the signalling and antiviral properties of SDF–1–derived small peptides", *Current Biology*, 8:369–376 (1998).
Luo, Z., Butcher, D., and Huang, Z., "Molecular Modeling of Interleukin–8 Receptor β and Analysis of the Receptor–ligand", *Interaction Protein Eng.*, 10:1039–1045 (1997).
Crump et al., "Solution structure and basis for functional activity of stromal cell–derived factor–1; dissociation of CXCR4 activation of stromal cell–derived factor–1; dissociation of CXCR4 activation from binding and inhibition of HIV–1", *The EMBO Journal*, 16:6996–7007 (1998).
Kontoyianni, M., and Lybrand, T.P., "Computer Modeling Studies of G Protein Coupled Receptors", *Med. Chem. Res.*, 3:407–418 (1993).
Picard et al., "Role of the amino–terminal extracellular domain of CXCR4 in human immunodeficiency virus type 1 entry", *Virology*, 231:105–11 (1997).

* cited by examiner

Primary Examiner—James Housel
Assistant Examiner—Ulrike Winkler
(74) Attorney, Agent, or Firm—Drinker Biddle & Reath LLP

(57) ABSTRACT

Synthetic peptide analogs of chemokines are designed to include the N- and C-terminal portions of the corresponding naturally occurring chemokine. In particular, synthetic peptide analogs of stromal cell-derived factor-1 (SDF-1) are effective in inhibiting HIV-1 entry and infection via the CXC chemokine receptor 4 (CXCR4). Each peptide comprises a peptide segment analog of the SDF-1 N-terminal region joined to a peptide segment analog of the SDF-1 C-terminal region. The peptides are useful for HIV treatment and prophylaxis.

8 Claims, 1 Drawing Sheet

CHEMOKINE-DERIVED SYNTHETIC PEPTIDES

CROSS-REFERENCE TO RELATED APPLICATION

The benefit of the filing date of U.S. provisional patent application Ser. No. 60/128,106, filed Apr. 7 1999, is hereby claimed. The entire disclosure of the aforesaid provisional application is incorporated herein by reference.

REFERENCE TO GOVERNMENT GRANT

This invention was made in the course of research sponsored by the National Institutes of Health grant GM57761. The U.S. Government has certain rights in the invention.

FIELD OF THE INVENTION

The invention relates to the field of synthetic peptides derived from chemokines. In particular, the invention relates to antiviral agents useful for inhibiting the infectivity of human acquired immunodeficiency virus. More particularly, the present invention is directed to synthetic peptides capable of inhibiting HIV-1 infection.

BACKGROUND OF THE INVENTION

Chemoattractant cytokines or "chemokines" are a group of proteins characterized by a fairly high degree of amino acid sequence conservation. They are chemoattractants for leukocytes. The chemotactic effect of substances on leukocytes may be determined by devices such as the chemotaxis chamber invented by Boyden (Boyden, *J. Ex. Med.* 115:453–66, 1962).

Chemokines act on responsive leukocytes subsets through chemokine receptors. Engagement of chemokine receptors results ultimately in the movement of the cell. Chemokine receptors belong to the superfamily of G-protein coupled receptors (GPCR) that possess seven transmembrane helices (Murphy, P. M., *Annu. Rev. Immunol.* 12:593–633, (1994). The three-dimensional structure of chemokine receptors is not known since currently no crystal structure is available for any of GPCR proteins (Strader et al., *Annu. Rev. Biochem.* 63:101–32, (1994); Kobilka, B., *Annu. Rev. Neurosci* 15:87-114, (1992)).

Chemokines are the natural ligands for chemokine receptors and are 8–10 kDa molecules which act as chemoattractants by signaling through their receptors and activating the target cells (Premack et al., *Nature Medicine* 2:1174–8, (1996)). Chemokines may be divided into at least three structural branches: C, CC, and CXC, according to variations in a shared cysteine motif (Schall, *Curr. Opin. Immunol.* 6:865–873,1994). The CX, also known as a, and the CC, also known as β, are the major classes of chemokines. Most CXC chemokines (those that contain an ELR sequence N-terminal to the CXC motif) are chemoattractants for neutrophils but not monocytes, whereas CC chemokines generally attract monocytes and lymphocytes, but not neutrophils. Basophils and eosinophils are affected predominantly by CC chemokines. The C chemokines appear to be lymphocyte specific.

Stromal-cell-derived factor-1 (SDF-1) is a member of the CXC chemokine family and is the ligand for CXC chemokine receptor 4 (CXCR4) (Tashiro et al., *Science* 261:600–603, (1993); Shirozu et al., *Genomics* 28:495–500, (1995)). The CC chemokines MIP-1β (macrophage inflammatory protein 1β), MIP-1a (macrophage inflammatory protein 1a) and RANTES (regulated on activation normal T cell expressed and secreted) bind CCR5.

Human immunodeficiency virus type 1 (HIV-1) enters cells through a fusion process in which the HIV-1 envelope glycoprotein gp 120 binds to CD4, the main receptor for HIV-1 on the cell surface. However, it has been known that CD4 alone is not sufficient for HIV-1 fusion and entry and that additional receptors may be needed (Maddon et al., *Cell* 47:333–348, (1986); Clapham et al., *Virology* 181:703–15, (1991)).

The chemokine receptors CXCR4 and CCR5 have been shown to be the long-sought coreceptors for non-syncytium-inducing and syncytium-inducing HIV-1 strains, respectively (Feng et al., *Science* 272:872–877, (1996); Deng et al., *Nature* 381:661–666, (1996); Dragic et al., *Nature* 381:667–673, (1996); Alkhatib et al., *Science* 272:1955–8, (1996)). While all HIV-1 strains appear to require either CXCR4, CCR5 or both (Zhang et al., *Nature* 383:768, (1996); Simmons et al., *Journal of Virology* 70:8355–60, (1996)), some strains can also use other chemokine receptors CCR3 and CCR2b as coreceptors for fusion and infection (Doranz et al., *Cell* 85:1149–58, (1996); Choe et al., *Cell* 85:1135–48, (1996)).

SDF-1 and CXCR4 play a role in HIV-1 viral entry. The fusion process may involve the initial binding of HIV-1 gp 120 to its high-affinity receptor CD4 which results in conformational changes in gp 120 and possibly also CD4 (Gershoni et al., *Journal* 7:1185–7, (1993); Clements et al., *AIDS Research & Human Retroviruses* 7:3–16. (1991); Sattentau et al., *Journal of Virology* 67:7383–93, (1993)). The gp 120-CD4 complex interacts with CXCR4 or other chemokine coreceptors to form a heterotrimeric complex of gp 120-CD4-coreceptor (Lapham et al., *Science* 274:602–5, (1996); Wu et al., *Nature* 6605:179–83, (1996); Trkola et al., *Nature* 384:184–7, (1996)). It has been shown that the HIV envelope can bind CXCR4 independently and that this interaction is enhanced by the presence of CD4 (Bandres et al., *Journal of Virology* 72:2500–2504, (1998).

On the other hand, it is also known that the CXCR4 ligand, SDF-1 inhibits HIV-1 infection (Bleul et al., *Nature* 382:829–833, (1996); Oberlin et al., *Nature* 382:833–835, (1996)).

Several inhibitors of HIV-1 have been found to target the coreceptor CXCR4 (Murakami et al., *J. Exp. Med.* 186:1389–133, (1997); Schols et al., *J. Exp. Med.* 186:1383–1388, (1997); Donzella et al., *Nature Medicine* 4:72–77, (1998); Doranz et al., *J. Exp. Med.* 186:1395–1400, (1997)). Synthetic peptides derived from SDF-1 have been shown to posses anti-HIV activity (Heveker etal., *Current Biology* 8:369–376 (1998)). While the solution structure of SDF-1 has been determined (Crump et al., *EMBO J.* 16:6996–7007 (1998)), there is no crystal structure available for CXCR4 to facilitate design of further inhibitors of HIV-1 binding to CXCR4.

There is a need for antiviral agents which can block HIV-1 entry via CXCR4. Preferably, but not necessarily, such peptides would not block the ability of CXCR4 to bind its natural ligand, SDF-1.

Ideally, selective inhibitors of HIV infection should comprise small molecule drugs. In contrast to other large protein-based therapeutics such as monoclonal antibodies, such small agents are advantageous since they are more likely to be non-immunogenic, orally administrable, and amenable for chemical synthesis and modification.

There is further need for improved chemokine peptides useful as therapeutic agents which provide enhanced activity and/or stability over existing chemokine peptides.

SUMMARY OF THE INVENTION

It is an object of the invention to provide antiviral synthetic peptides capable of inhibiting HIV-1 infection, by inhibiting HIV-1 mediated cytopathogenesis and cell fusion.

It is an object to provide a method of treating or inhibiting HIV-1 infection, by administration of the synthetic peptides.

It is an object of the invention to provide other synthetic chemokine peptides with enhanced properties.

The antiviral compounds of the present invention are in the form of peptides which possess anti-HIV activity. They inhibit HIV-1 entry into HIV-1 infection susceptible cells via the CXC chemokine receptor 4.

In all embodiments, the peptide may optionally comprise an amino-terminal and/or carboxy-terminal protecting group.

According to one embodiment, the invention is a peptide of the formula $$X_1\text{-A-B-C-D-}X_2\text{-E-F-G-}X_3\text{-L-}X_4\text{-J-K-M-N-P-Q-R-S-T-V-Ala-W-Y-}X_5 \quad (I)$$

wherein:

$X_1$ is from zero to eight amino acids, $X_2$ is three amino acids, $X_3$ is from zero to eight amino acids, L is a linker comprising a covalent bond or chemical moiety, $X_4$ is from zero to eight amino acids, $X_5$ is from zero to eight amino acids, A is Ile, Leu, Phe or Val, B is Ser or Thr C is Phe, Tyr, or Trp, D is Arg, His or Lys, E is Arg, His or Lys, F is Phe, Tyr, Trp or Leu G is Phe, Tyr, Trp or Leu J is Ile, Leu, Phe or Val, K is Arg, Lys or His, M is Phe, Tyr or Trp N is Ile, Leu, Phe or Val, P is Asn, Asp, Glu or Gin Q is Asn, Asp, Glu or Gin R is Tyr, Trp or Phe, S is Ile, Leu, Phe or Val, T is Asn, Asp, Glu or Gin V is Arg, Lys or His, W is Ile, Leu, Phe or Val, Y is Asn, Asp, Glu or Gln, and said peptide optionally comprises an amino-terminal and/or carboxy-terminal protecting group.

In preferred embodiments, A is Leu, B is Ser, C is Tyr, D is Arg, E is Arg, F is Phe, G is Phe, J is Leu, K is Lys, M is Trp, N is Ile, P is Gln, Q is Glu, R is Tyr, S is Leu, T is Glu, V is Lys, W is Leu and/or Y is Asn.

In preferred embodiments, each of $X_1$, $X_3$, $X_4$, and $X_5$ is from zero to six amino acids, preferably zero to four amino acids.

In the foregoing embodiments of the invention, it should be understood that each amino acid of the segments $X_1$, $X_2$, $X_3$, $X_4$, and $X_5$ may comprise, independent of any other amino acid in the segment, any amino acid.

According to another preferred embodiment, $X_1$ is (i) zero amino acids, or (ii) the segment $A^1$-$B^1$-$C^1$-$D^1$ or N-terminal truncation fragment thereof containing at least one amino acid, wherein:

$A^1$ is Arg, Lys or His, $B^1$ is Pro or N-methylaianine, $C^1$ is Ile, Leu, Phe or Val, and $D^1$ is Ser or Thr;

$X_3$ is (i) zero amino acids, or (ii) the segment $A^2$-$B^2$-$^2$-$D^2$-Ala-$E^2$-Ala-$F^2$, or C-terminal truncation fragment thereof containing at least one amino acid, wherein:

$A^2$ is Asn, Asp, Glu or Gln, $B^2$ is Ser or Thr, $C^2$ is Arg, Lys or His, $D^2$ is Ile, Leu, Phe or Val, $E^2$ is Arg, Lys or His, $F^2$ is Asn, Asp, Glu or Gln;

$X_4$ is (i) zero amino acids, or (ii) the segment $A^3$-$B^3$-$C^3$-$D^3$, or N-terminal truncation fragment thereof containing at least one amino acid, wherein:

$A^3$ is Ile, Leu, Phe or Val, $B^3$ is Asn, Asp, Glu or Gln, $C^3$ is Pro or N-methylaianine, $D^3$ is Arg, Lys or His; and $X_5$ is zero amino acids.

According to another preferred embodiment, L is an amino acid sequence containing from 2 to 10 amino acids, more preferably from 2 to 6 amino acids, most preferably from 2 to 4 amino acids. In some embodiments of the invention, the amino acid sequence L comprises glycine or lysine amino acids.

In some embodiments, $X_2$ is Cys-Pro-Cys.

According to other embodiments,

A-B-C-D is Leu-Ser-Tyr-Arg (SEQ ID NO:11),

E-F-G is Arg-Phe-Phe

J-K-M-N-P-Q-R-S-T-V is Leu-Lys-Trp-Ile-Gln-Glu-Tyr-Leu-Glu-Lys (SEQ ID NO:12), and W-Y is Leu-Asn.

According to other embodiments, the segment $A^1$-$B^1$-$C^1$-$D^1$ is Lys-Pro-Val-Ser (SEQ ID NO:1) or N-terminal truncation fragment thereof containing at least one amino acid;

the segment $A^2$-$B^2$-$C^2$-$D^2$-Ala-$E^2$-Ala-$F^2$ is Glu-Ser-His-Val-Ala-Arg-Ala-Asn (SEQ ID NO:2), or C-terminal truncation fragment thereof containing at least one amino acid; and the segment $A^3$-$B^3$-$C^3$-$D^3$ is Ile-Asp-Pro-Lys (SEQ ID NO:3), or C-terminal truncation fragment thereof containing at least one amino acid.

A pharmaceutical composition comprises a pharmaceutically acceptable carrier and a peptide according to the invention.

A method of inhibiting entry of HIV-1 into CXCR4-expressing cells comprises contact the cells with a peptide according to the invention.

A method of inhibiting infection by HIV-1 comprises administering to an individual an effective amount of a peptide according to the invention.

According to another embodiment of the invention, a synthetic chemokine peptide is provided. The peptide comprises an N-terminal segment comprising a sequence of from 10 to 25 amino acids having at least 50% sequence identity with a first reference segment of a naturally occurring chemokine, said first reference segment being found in the N-terminal region of said naturally occurring chemokine. The peptide further comprises a C-terminal segment comprising a sequence of from 10 to 25 amino acids having at least 50% sequence identity with a second reference segment of the naturally occurring chemokine, said second first reference segment being found in the C-terminal region of the naturally occurring chemokine. The N-terminal and C-terminal segments of the synthetic peptide are connected by a linker L as defined above. The linker links the C-terminus of the synthetic peptide N-terminal segment to the N-terminus of the synthetic peptide C-terminal segment. Preferably, the degree of sequence identity between each segment of the synthetic peptide and the corresponding first or second reference sequence of the naturally occurring chemokine is at least about 70%, more preferably at least about 80%, most preferable about 90%. In preferred embodiments, the amino acid sequence of the N-terminal segment differs, if at all, from the first reference segment of the naturally occurring chemokine only by conservative amino acid substitutions, and the amino acid sequence of the C-terminal segment differs, if at all, from the second reference segment of the naturally occurring chemokine only by conservative amino acid substitutions.

Other aspects and advantages of the present invention are described in the drawings and in the following detailed description of the preferred embodiments thereof.

Abbreviations and Short Forms

"CXCR4" means CXC chemokine receptor 4.
"HIV-1" means human immunodeficiency virus type 1.
"SDF-1" means stromal cell-derived factor-1.

Amino Acid Abbreviations

The nomenclature used to describe polypeptide compounds of the present invention follows the conventional practice wherein the amino group is presented to the left and the carboxy group to the right of each amino acid residue. In the formulae representing selected specific embodiments of the present invention, the amino-and carboxy-terminal groups, although not specifically shown, will be understood to be in the form they would assume at physiologic pH values, unless otherwise specified. In the amino acid structure formulae, each residue is generally represented by a three-letter designation, corresponding to the trivial name of the amino acid, in accordance with the following schedule:

| | |
|---|---|
| Alanine | Ala |
| Cysteine | Cys |
| Aspartic Acid | Asp |
| Glutamic Acid | Glu |
| Phenylalanine | Phe |
| Glycine | Gly |
| Histidine | His |
| Isoleucine | Ile |
| Lysine | Lys |
| Leucine | Leu |
| Methionine | Met |
| Asparagine | Asn |
| Proline | Pro |
| Glutamine | Gln |
| Arginine | Arg |
| Serine | Ser |
| Threonine | Thr |
| Valine | Val |
| Tryptophan | Trp |
| Tyrosine | Tyr |

Definitions

The following definitions, of terms used throughout the specification, are intended as an aid to understanding the scope and practice of the present invention.

A "peptide" is a compound comprised of amino acid residues covalently linked by peptide bonds.

The expression "amino acid" as used herein is meant to include both natural and synthetic amino acids, and both D and L amino acids. "Natural amino acid" means any of the twenty primary, naturally occurring amino acids which typically form peptides, polypeptides, and proteins. "Synthetic amino acid" means any other amino acid, regardless of whether it is prepared synthetically or derived from a natural source. As used herein, "synthetic amino acid" also encompasses chemically modified amino acids, including but not limited to salts, derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half life without adversely affecting their activity. Additionally, a disulfide linkage may be present or absent in the peptides of the invention, as long as anti-HIV activity is maintained.

Amino acids have the following general structure:

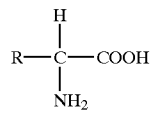

Amino acids are classified into seven groups on the basis of the side chain R: (1) aliphatic side chains, (2) side chains containing a hydroxylic (OH) group, (3) side chains containing sulfur atoms, (4) side chains containing an acidic or amide group, (5) side chains containing a basic group, (6) side chains containing an aromatic ring, and (7) proline, an imino acid in which the side chain is fused to the amino group. Peptides comprising a large number of amino acids are sometimes called "polypeptides". The amino acids of the peptides described herein and in the appended claims are understood to be either D or L amino acids with L amino acids being preferred.

As used herein, "protected" with respect to a terminal amino group refers to a terminal amino group of a peptide, which terminal amino group is coupled with any of various amino-terminal protecting groups traditionally employed in peptide synthesis. Such protecting groups include, for example, acyl protecting groups such as formyl, acetyl, benzoyl, trifluoroacetyl, succinyl, and methoxysuccinyl; aromatic urethane protecting groups such as benzyloxycarbonyl; and aliphatic urethane protecting groups, for example, tert-butoxycarbonyl or adamantyloxycarbonyl. See Gross and Mienhofer, eds., The Peptides, vol. 3, pp. 3–88 (Academic Press, New York, 1981) for suitable protecting groups.

As used herein, "protected" with respect to a terminal carboxyl group refers to a terminal carboxyl group of a peptide, which terminal carboxyl group is coupled with any of various carboxyl-terminal protecting groups. Such protecting groups include, for example, tert-butyl, benzyl or other acceptable groups linked to the terminal carboxyl group through an ester or ether bond.

By "synthetic chemokine peptide" is meant a peptide having an amino acid sequence, substantial portions of which are the same as or homologous to portions of the amino acid sequence of a naturally occurring chemokine.

By "N-terminal segment" or "N-terminal portion" is meant a part of a peptide or mature polypeptide which terminates in the N-terminal amino acid of the peptide or polypeptide.

By "C-terminal segment" or "C-terminal portion" is meant a part of a peptide or a mature polypeptide which terminates in the C-terminal amino acid or polypeptide.

By "N-terminal truncation fragment" with respect to an amino acid sequence is meant a fragment obtained from a parent sequence by removing one or more amino acids from the N-terminus thereof.

By "C-terminal truncation fragment" with respect to an amino acid sequence is meant a fragment obtained from a parent sequence by removing one or more amino acids from the C-terminus thereof.

DETAILED DESCRIPTION OF THE INVENTION

Figure 1:
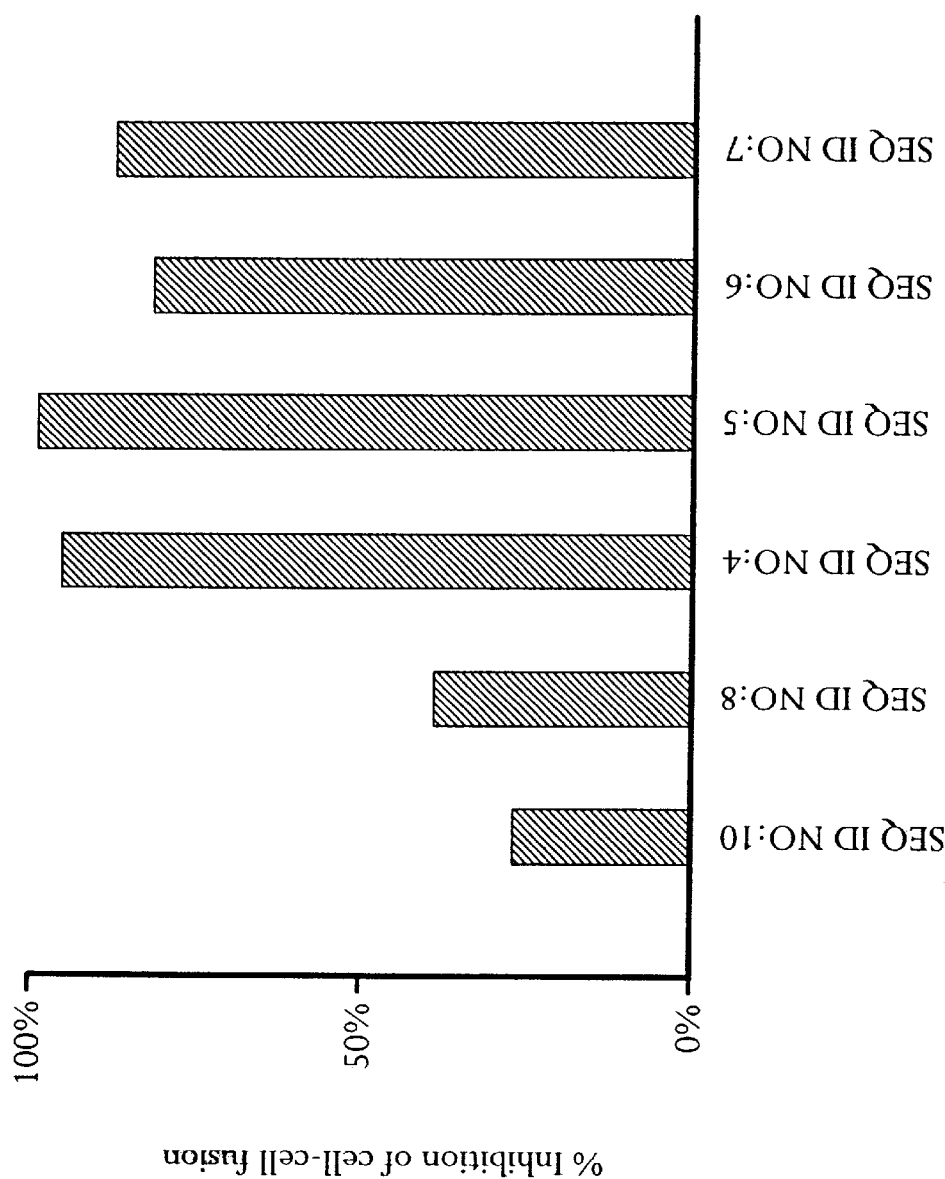
FIG. 1 is a bar graph of the percent inhibition of cell fusion of the peptides of the invention (SEQ ID NO:4–7) compared to peptides corresponding to the SDF-1 N-terminus (SEQ ID NO:8, 10) in an HIV-1 gp 120-CXCR4-mediated cell fusion assay.

According to the present invention, synthetic peptides have been designed based upon a previously unknown model of the CXCR4-SDF-1 complex. These peptides inhibit HIV-1 viral entry via CXCR4 in a concentration dependent manner. The peptides inhibit infectivity of HIV-1. Hence, the peptides are useful as therapeutics for reducing ongoing viral infection, or as prophylactics for inhibiting viral infection, particularly infection of CXCR4+cells.

Using a molecular modeling approach, a proposed structure was constructed for the transmembrane helices of CXCR4. This model indicates that the N-terminal region of CXCR4 plays a critical role in recognizing SDF-1 and contributes the most in terms of ligand binding energy. In addition to the N-terminus in both receptor and ligand, the role of other regions such as ECL2 and ECL3 of CXCR4 and the C-terminal helix of SDF-1 was also revealed in the structural model. This model permitted, for the first time, the identification of putative binding sites in SDF-1, and the design of novel peptides comprising both N- and C-termini of SDF-1. The peptides are inhibitors of CXCR4 mediated HIV-1 fusion. They inhibit HIV-1 transmission to uninfected cells.

The antiviral activity of any SDF1-derived peptide of the invention may be measured by a convenient in vitro cell-cell fusion assay. An HIV-1 gp 120-CXCR4 mediated cell-cell fusion assay is used to test the effect of peptides on HIV-1 virus entry via CXCR4. For the assay, HIV-1 Env proteins and T7 RNA polymerase were introduced into effector 293 cells by infection with recombinant vaccinia virus at a multiplicity of infection of 10 for 2 hours. QT6 target cells were transfected in 6-well plates with plasmids encoding CD4, CXCR4 and luciferase under control of T7 promoter, using the calcium phosphate precipitation method. The effector and target cells were then subjected to fusion conditions in the presence of peptide. Following fusion, the cells were lysed in reporter lysis buffer and assayed for luciferase activity using commercially available reagents.

An HIV-induced syncytia assay may also be utilized to testthe antiviral activity of the SDF1-derived peptides of the invention. Accordingly, uninfected CD4+cells (such as Molt or CEM cells, for example) are cultured in the presence of chronically HIV-infected cells and peptide. The conditions for HIV-induced syncytia formation assays are well-known to those skilled in the art. See e.g. U.S. Pat. No. 5,464,933, incorporated herein by reference. The culture is examined for the presence of multinucleated giant cells, which are indicative of cell fusion and syncytia formation.

In addition to the cell-cell fusion assay, the binding of the peptides of the invention to CXCR4 was also characterized by a fluorescence-activated cell sorter (FACS) analysis. 293 cells transfected with CXCR4 and a FITC conjugated antibody against CXCR4, 12D5 (Endres et al., *Cell* 87:745–756, (1996)) were used for the assay. Another FITC conjugated antibody against CCR5, 12D1 (Doranz et al., *Cell* 85:1149–58, (1996)) was used as a negative control. FITC-12D1 against CCR5 showed no binding to 293 cells transfected with CXCR4, whereas FITC-12D5 against CXCR4 exhibited strong binding. Peptides of the present invention significantly blocked the binding of 12D5 to CXCR4, whereas a control peptide analog of MIP-1β had no effect. These results provide further evidence for the involvement in CXCR4 binding of both N-and C-termini of SDF-1.

Each SDF1-derived peptide of the invention comprises a first segment which mimics the N-terminal binding site of SDF-1 for CXCR4 and a second segment which mimics the C-terminal binding site of SDF-1 for CXCR4. The segments are joined by a linker. The peptides possess enhanced receptor binding and inhibition of HIV-1 entry. The peptides of the invention are characterized by enhanced activity over separate peptides derived only from the N-terminal region of SDF-1, or derived only from the C-terminal region of SDF-1.

The N-terminal segment of the peptides comprise a core segment $A$-$B$-$C$-$D$-$X_2$-$E$-$F$-$G$ substantially corresponding to amino acids 5-14 of the native SDF-1 native amino acid sequence. Amino acids A, B, C, and D represent the corresponding native amino acids Leu, Ser, Tyr and Arg, respectively, or conservative substitutions thereof. $X_2$ is any three amino acids, preferably the native sequence Cys-Pro-Cys. Amino acids E, F and G represent the corresponding native amino acids Arg, Phe and Phe, respectively, or conservative substitutions thereof. Conservative amino acid substitutions typically include substitutions within the following groups: glycine and alanine; valine, isoleucine and leucine; aspartic acid and glutamic acid; asparagine and glutamine; serine and threonine; lysine and arginine; phenylalanine and tyrosine.

The core segment within the larger N-terminal segment may be flanked by a segment $X_1$ containing up to eight additional amino acids upstream (i.e., in the N-terminal direction) of the core segment, and a segment $X_3$ containing up to eight additional amino acids downstream (i.e., in the C-terminal direction) of the core segment. Preferably, $X_1$ is a segment of four amino acids $A^1$-$B^1$-$C^1$-$D^1$, or N-terminal truncation fragment thereof) corresponding to amino acids 1–4 of the native SDF-1 native amino acid sequence. Amino acids $A^1$, $B^1$, $C^1$ and $D^1$ represent the corresponding native amino acids Lys, Pro, Val and Ser, respectively, or conservative substitutions thereof. Preferably, $X_3$ is a segment of eight amino acids $A^2$-$B^2$-$C^2$-$D^2$-Ala-$E^2$-Ala-$F^2$ (or C-terminal truncation fragment thereof) corresponding to amino acids 15–22 of the native SDF-1 native amino acid sequence. Amino acids $A^2$, $B^2$, $C^2$, $D^2$, $E^2$ and $F^2$ represent the corresponding native amino acids Glu, Ser, His, Val, Arg and Asn, respectively, or conservative substitutions thereof. The core segment $A$-$B$-$C$-$D$-$X_2$-$E$-$F$-$G$ and the optional flanking segments $X_1$ and $X_3$ form the complete N-terminal segment of the peptides of the invention.

The C-terminal segment of the present peptides comprises a core segment J-K-M-N-P-Q-R-S-T-V-Ala-W-Y corresponding to amino acids 55–67 of the native SDF-1 native amino acid sequence. Amino acids J, K, M, N, P, Q, R, S, T, V, W and Y represent the corresponding native amino acids Leu, Lys, Trp, Ile, Gly, Glu, Tyr, Leu, Glu, Lys, Leu and Asn, respectively, or conservative substitutions thereof.

The core segment within the larger C-terminal segment may be flanked by a segment $X_4$ containing up to eight additional amino acids upstream of the core segment, and a segment $X_5$ containing up to eight additional amino acids downstream of the core segment. Preferably, $X_4$ is a segment of four amino acids $A^3$-$B^3$-$C^3$-$D^3$ (or N-terminal truncation fragment thereof) corresponding to amino acids 51–54 of the native SDF-1 amino acid sequence. Amino acids $A^3$, $B^3$, $C^3$ and $D^3$ represent the corresponding native amino acids Ile, Asp, Pro and Lys, respectively, or conservative substitutions thereof. Preferably, $X_5$ is zero amino acids. The core segment J-K-M-N-P-Q-R-S-T-V-Ala-W-Y and the optional flanking segments $X_4$ and $X_5$ form the complete C-terminal segment of the peptides of the invention.

In the broadest embodiment of the SDF1 peptides of the invention, flanking sequences $X_1$, $X_3$, $X_4$, $X_5$ may comprise any amino acid. However, these flanking segments are preferably derived from the native SFD-1 sequence, and thus duplicate the native amino acid sequence of SFD-1, or comprise conservative amino acid substitutions of one or more native amino acids.

The linker connecting the SDF-1 N-terminal and C-terminal peptide segments forming the peptides of the invention may comprise a covalent bond or a chemical moiety. The linker may comprise any chemical group which is compatible with the peptide segments being linked and which does not adversely affect the binding of the peptide to the CXCR4 receptor. The linker is preferably flexible, and maintains the relative spatial geometry of the two segments of the peptide. Preferably, the spacer is a segment comprising a series of amino acids, most preferably form 2 to ten amino acids, most preferably from 2 to six amino acids. According to one preferred embodiment of the invention, the linker comprises glycine or lysine amino acids, such as the segment Gly-Gly-Gly-Gly or Lys-Lys-Lys-Lys. Glycine residues are particularly preferred as they maintain the relative spatial geometry of the N-terminal and C-terminal SDF-1 analogs, and provide flexibility to this bridge.

According to one embodiment of the invention, the linker is a peptide bond. Hence, the connection between the SDF-1 N-terminal and C-terminal peptide segments in this embodiment is a peptide bond joining the C-terminal amino acid residue of the N-terminal peptide segment and the N-terminal amino acid residue of the C-terminal peptide segment.

Preferred SDF1-derived peptides according to the present invention inhibit, at a concentration of no more than 25 $\mu$M, greater than 50% (preferably greater than 75%) of the binding of (i) gp 120-expressing 293 cells transfected to express T7 RNA polymerase and (ii) human CD4-expressing QT6 cells transfected to express CD4 and the CXCR4. Such a cell-cell binding assay is described in Example 1, below.

According to another embodiment of the invention, a similar strategy is employed to prepare synthetic peptides based upon the amino acid sequences of other chemokines. For a review of chemokines and their receptors, and their classification, see Premack & Schall, *Nature Medicine* 2(11) :1174–1178 (1996), the entire disclosure of which is incorporated herein by reference. The N-terminal region of a chemokine is the principal site by which the chemokine interacts with its receptor, and is therefore primarily responsible for the chemokine's biological activity. It is believed that the C-terminal region of the molecule plays a role in recruiting the chemokine to the cell surface where the chemokine receptor is located. The C-terminal region also plays a role in stabilizing the chemokine once bound to the receptor. Stabilization includes prevention of enzyme hydrolysis of the chemokine, so that the chemokine maintains its signaling function once bound to the receptor.

While chemokine synthetic peptides have been prepared, they are typically based upon the chemokine N-terminal amino acid sequence to mimic the receptor binding site on the chemokine. Such peptides therefor omit the beneficial recruitment and stabilization functions of the chemokine C-terminal domain.

According to the present invention, chemokine synthetic peptides are provided. Each such synthetic peptide comprises a first (N-terminal) segment which mimics the N-terminal region of the corresponding naturally occurring full-length chemokine polypeptide. The N-terminal segment of the synthetic chemokine peptide contains or mimics the binding site for the corresponding chemokine receptor.

Each synthetic chemokine peptide further comprises a second (C-terminal) segment which mimics the C-terminal region of the corresponding naturally occurring full-length chemokine polypeptide. The C-terminal segment is available to perform the recruitment and stabilization functions of the C-terminal region of the full-length chemokine polypeptide.

The result of this N-terminal/C-terminal segment construction is a synthetic molecule incorporating the major functional characteristics of the corresponding naturally occurring chemokine. It is expected, as demonstrated in the case of the synthetic SDF-1 peptides described herein, that other synthetic chemokine peptides based upon this construction will have enhanced biological activity over peptide analogs modeled from the native N-terminal region alone.

The N-terminal segment of the inventive peptides comprises a sequence of from about 10 to about 25, more preferably from about 10 to about 20, most preferably from about 10 to about 15, amino acids from a reference segment of approximately the same length forming the N-terminal portion of the corresponding naturally occurring chemokine. Similarly, the C-terminal segment of the inventive peptides comprises a sequence of from about 10 to about 25, more preferably from about 10 to about 20, most preferably from about 10 to about 15, amino acids from a reference segment of approximately the same length forming the C-terminal portion of the corresponding naturally occurring chemokine. The amino acid sequence of the segments is identical to the corresponding chemokine native amino sequence portions, or one or more positions may be substituted with other amino acids. The substitutions preferably comprise conservative amino acid substitutions. According to one embodiment of the invention, each segment has at least 50%, preferably at least 70%, more preferably at least 80%, most preferably at least 90%, sequence identity with the corresponding native chemokine portion of the same length. By "sequence identity" is meant the same amino acids in the same relative positions. The segments are connected by a linker as described above.

The synthetic chemokine peptides may be synthesized utilizing the known amino acid sequences of the various known chemokines. The following is a partial list of human chemokines and the corresponding GenBank accession numbers for GenBank records providing the nucleotide (DNA or mRNA) and encoded amino acid sequences. Each GenBank record is incorporated herein by reference. "NID" is the National Center for Biotechnology and Information sequence identifier. By "cds" is meant coding sequence.

| Chemokines GenBank Record | Accession No. | NID |
|---|---|---|
| Human eotaxin precursor mRNA, complete cds | U46573 | g1280140 |
| Human monocyte chemoattractant protein-4 precursor (MCP-4) mRNA, complete cds | U46767 | g1732122 |
| Human pre-B cell stimulating factor homologue (SDF1a) mRNA, complete cds | L36034 | g1220363 |
| Human pre-B cell stimulating factor homologue (SDF1b) mRNA, complete cds | L36033 | g1220365 |
| Human mRNA for EBI1-ligand chemokine, complete cds | AB000887 | g2189952 |
| Human DNA for SCM-1beta precursor, complete cds | D63789 | g1754608 |
| Human DNA for SCM-1alpha precursor, complete cds | D63790 | g1754610 |
| Human mRNA for CC chemokine LARC precursor, complete NID | D86955 | G1871138 |
| Human macrophage-derived chemokine precursor (MDC) mRNA, complete cds | U83171 | g1931580 |
| Human CC chemokine STCP-1 mRNA, complete cds | U83239 | g2062424 |
| Human CX3C chemokine precursor, mRNA, alternatively spliced, complete cds | U84487 | g1888522 |
| Human myeloid progenitor inhibitory factor-1 MPIF-1 mRNA, complete cds | U85767 | g1916249 |
| Human myeloid progenitor inhibitory factor-1 MPIF-2 mRNA, complete cds | U85768 | g1916251 |
| Human chemokine (TECK) mRNA, complete cds | U86358 | g2388626 |
| Human beta chemokine Exodus-2 mRNA, complete cds | U88320 | g2196919 |
| Human beta chemokine Exodus-3 mRNA, complete cds | U88321 | g2196921 |
| Human CX3C chemokine precursor, mRNA, alternatively spliced, complete cds | U91835 | g1899258 |
| Human mRNA for chemokine, complete cds | D43767 | g1536878 |
| Human mRNA for eotaxin, complete cds | D49372 | g1552240 |
| Human eotaxin precursor gene, complete cds | U46572 | g2088508 |
| Human macrophage inflammatory protein 3 alpha (MIP-3a) mRNA, complete cds | U77035 | g1790924 |
| Human macrophage inflammatory protein 3 beta (MIP-3beta) mRNA, complete cds | U77180 | g1791002 |
| Human line-1 reverse transcriptase gene, partial cds, and granulocyte chemotactic protein-2 (GCP-2) gene, complete cds | U83303 | g1916228 |
| Human netrin-2 like protein (NTN2L) gene, complete cds | U86758 | g2052392 |
| Human Duffy blood group antigen (Fya-b+) mRNA, complete cds | U01839 | g425267 |
| Human herpesvirus 6 serotype B putative major immediate-early genes | U92288 | g2769711 |
| Human herpesvirus-6 (HIV-6) u1102, variant A, complete virion genome | X83413 | g853961 |
| Kaposi's sarcoma-associated herpesvirus BCK gene, complete cds | U83351 | g1778605 |
| Human C6 beta-chemokine mRNA, complete cds | U67128 | g4097705 |
| Human chemokine alpha 3 (CKA-3) mRNA, complete cds | U81234 | g4098960 |
| Human monocyte chemotactic protein-4 precursor (MCP-4) mRNA, complete cds | U59808 | g4097420 |
| Human chemokine (hmrp-2a) mRNA, complete cds | U58913 | g4204907 |
| Human chemokine (hmrp-2b) mRNA, complete cds | U58914 | g4204909 |
| H. sapiens mRNA for CC-chemokine. | Z69291 | g1181148 |
| H. sapiens mRNA for CC-chemokine, eotaxin variant (clone 34). | Z75669 | g1531980 |
| H. sapiens mRNA for CC-chemokine, eotaxin variant (clone 53). | Z75668 | g1531982 |
| H. sapiens gene for chemokine HCC-1. | Z49269 | g1004266 |
| H. sapiens mRNA for chemokine HCC-1. | Z49270 | g1004268 |
| H. sapiens Humig mRNA. X72755 | S60728 | g311375 |
| H. sapiens NC28 mRNA for monocyte chemoattractant protein (MCP-3). | X71087 | g288396 |
| H. sapiens mRNA for ATAC protein. | X86474 | g895846 |
| Human eotaxin precursor mRNA, complete cds. | U46573 | g1280140 |
| Human monocyte chemoattractant protein-4 precursor (MCP-4) mRNA, complete cds. | U46767 | g1732122 |
| Human pre-B cell stimulating factor homologue (SDF1a) mRNA, complete cds. | L36034 | g1220363 |

-continued

| Chemokines GenBank Record | Accession No. | NID |
|---|---|---|
| Human pre-B cell stimulating factor homologue (SDF1b) mRNA, complete cds. | L36033 | g1220365 |
| pro-inflammatory cytokine {promoter} [human, placenta, Genomic, 1016 nt]. | S64885 | g408870 |
| Duffy [human, Caucasian individual AZ, Fy(a-b−) phenotype, erythrocytes, Genomic Mutant, 88 nt]. | S79269 | g1086935 |
| *Homo sapiens* mRNA for CC chemokine, complete cds. | AB000221 | g2289718 |
| Human mRNA for EBI1-ligand chemokine, complete cds. | AB000887 | g2189952 |
| *Homo sapiens* mRNA for SLC, complete cds. | AB002409 | g2335034 |
| *Homo sapiens* mRNA for chemokine LEC precursor, complete cds. | AB007454 | g2723285 |
| *Homo sapiens* beta chemokine mRNA, complete cds. | AF001979 | g2624924 |
| *Homo sapiens* Angie mRNA, complete cds. | AF029894 | g3169813 |
| *Homo sapiens* MIP-1 delta mRNA, complete cds. | AF031587 | g2739163 |
| *Homo sapiens* monocyte chemoattractant protein 3 (MCP3) mRNA, partial cds. | AF043338 | g2905625 |
| *Homo sapiens* macrophage inflammatory protein 1 alpha (MIP1a) mRNA, partial cds. | AF043339 | g2905627 |
| *Homo sapiens* macrophage inflammatory protein 2 alpha (MIP2a) mRNA, partial cds. | AF043340 | g2905629 |
| *Homo sapiens* RANTES precursor, mRNA, complete cds. | AF043341 | g2905631 |
| *Homo sapiens* B lymphocyte chemoattractant BLC mRNA, complete cds. | AF044197 | g2911375 |
| *Homo sapiens* monotactin-1 mRNA, complete cds. | AF055467 | g3395775 |
| Human DNA for SCM-1beta precursor, complete cds. | D63789 | g1754608 |
| Human DNA for SCM-1alpha precursor, complete cds. | D63790 | g1754610 |
| Human mRNA for CC chemokine LARC precursor, complete cds. | D86955 | g1871138 |
| *Homo sapiens* CC chemokine DC-CK-1/PARC/MIP-4 gene, exon 1. | AF082212 | g3426358 |
| *Homo sapiens* CC chemokine DC-CK-1/PARC/MIP-4 gene, exon 2. | AF082213 | g3426359 |
| *Homo sapiens* CC chemokine DC-CK-1/PARC/MIP-4 gene, exon 3 and complete cds. | AF082214 | g3426360 |
| *Homo sapiens* mRNA for alternative activated macrophage specific CC chemokine 1. | Y13710 | g2326515 |
| *H. sapiens* mRNA for chemokine CC-2 and CC-1. | Z70292 | g1296608 |
| *Homo sapiens* cDNA for a CXC chemokine. | AJ002211 | g2832410 |
| *H. sapiens* MCP-2 gene. | X99886 | g1905800 |
| *H. sapiens* MCP-3 gene for monocyte chemotactic protein-3. | X72309 | g515869 |
| *H. sapiens* mRNA for monocyte chemoattractant protein 4. | X98306 | g2689216 |
| *Homo sapiens* chemokine exodus-1 mRNA, complete cds. | U64197 | g1778716 |
| Human macrophage-derived chemokine precursor (MDC) mRNA, complete cds. | U83171 | g1931580 |
| Human CC chemokine STCP-1 mRNA, complete cds. | U83239 | g2062424 |
| Human CX3C chemokine precursor, mRNA, alternatively spliced, complete cds. | U84487 | g1888522 |
| Human myeloid progenitor inhibitory factor-1 MPIF-1 mRNA, complete cds. | U85767 | g1916249 |
| Human myeloid progenitor inhibitory factor-1 MPIF-2 mRNA, complete cds. | U85768 | g1916251 |
| Human chemokine (TECK) mRNA, complete cds. | U86358 | g2388626 |
| Human beta chemokine Exodus-2 mRNA, complete cds. | U88320 | g2196919 |
| Human beta chemokine Exodus-3 mRNA, complete cds. | U88321 | g2196921 |
| *Homo sapiens* IL-10-inducible chemokine (HCC-4) mRNA, complete cds. | U91746 | g2581780 |
| Human CX3C chemokine precursor, mRNA, alternatively spliced, complete cds. | U91835 | g1899258 |
| *Homo sapiens* Chromosome 16 BAC clone CIT987SK-A-152E5, complete sequence. | AC004382 | g3252819 |
| Human mRNA for chemokine, complete cds. | D43767 | g1536878 |
| Human mRNA for eotaxin, complete cds. | D49372 | g1552240 |
| human mRNA for SCM-1 (single cysteine motif-1), complete cds. | D43768 | g927650 |

-continued

| Chemokines GenBank Record | Accession No. | NID |
|---|---|---|
| *Homo sapiens* gene for CC chemokine PARC precursor, complete cds. | AB012113 | g3869137 |
| *Homo sapiens* putative alpha chemokine (H174) mRNA, complete cds. | AF002985 | g2580585 |
| *Homo sapiens* interferon stimulated T-cell alpha chemoattractant precursor, mRNA, complete cds. | AF030514 | g3219692 |
| *Homo sapiens* putative small inducible subfamily B-type cytokine (SCYB9B) gene, partial cds. | AF053972 | g3746491 |
| *Homo sapiens* CC chemokine gene cluster, complete sequence. | AF088219 | g3719360 |
| *Homo sapiens* mRNA for monocyte chemotactic protein-3 (MCP-3). | X72308 S57464 | g3928270 |
| Human eotaxin precursor gene, complete cds. | U46572 | g2088508 |
| Human macrophage inflammatory protein 3 alpha (MIP-3a) mRNA, complete cds. | U77035 | g1790924 |
| Human macrophage inflammatory protein 3 beta (MIP-3beta) mRNA, complete cds. | U77180 | g1791002 |
| Human line-1 reverse transcriptase gene, partial cds, and granulocyte chemotactic protein-2 (GCP-2) gene, complete cds. | U83303 | g1916228 |
| Human netrin-2 like protein (NTN2L) gene, complete cds. | U86758 | g2052392 |
| Human Duffy blood group antigen (Fya-b+) mRNA, complete cds. | U01839 | g425267 |
| HIV-1 patient AB28 from Argentina, envelope glycoprotein (env) gene, partial cds. | AF001428 | g2105008 |
| HIV-1 patient CD65 from Argentina, envelope glycoprotein (env) gene, partial cds. | AF001429 | g2105010 |
| HIV-1 patient CS93 from Argentina, envelope glycoprotein (env) gene, partial cds. | AF001430 | g2105012 |
| HIV-1 patient FS3 from Argentina, envelope glycoprotein (env) gene, partial cds. | AF001431 | g2105014 |
| HIV-1 child B136 JA3613 isolate from Italy, envelope glycoprotein V3 region (env) gene, partial cds. | AF023305 | g3642779 |
| HIV-1 child B136 J6366 isolate from Italy, envelope glycoprotein V3 region (env) gene, partial cds. | AF023306 | g3642781 |
| HIV-1 child B136 J57 isolate from Italy, envelope glycoprotein V3 region (env) gene, partial cds. | AF023307 | g3642788 |
| HIV-1 child B136 J108 isolate from Italy, envelope glycoprotein V3 region (env) gene, partial cds. | AF023308 | g3642790 |
| HIV-1 child B136 J130 isolate from Italy, envelope glycoprotein V3 region (env) gene, partial cds. | AF023309 | g3642793 |
| HIV-1 child B145 J3284 isolate from Italy, envelope glycoprotein V3 region (env) gene, partial cds. | AF023310 | g3642795 |
| HIV-1 child B145 J5508 isolate from Italy, envelope glycoprotein V3 region (env) gene, partial cds. | AF023311 | g3642797 |
| HIV-1 child B145 J34 isolate from Italy, envelope glycoprotein V3 region (env) gene, partial cds. | AF023312 | g3642800 |
| HIV-1 child B145 J132 isolate from Italy, envelope qlycoprotein V3 region (env) gene, partial cds. | AF023313 | g3642802 |
| HIV-1 child B193 JA4200 isolate from Italy, envelope glycoprotein V3 region (env) gene, partial cds. | AF023314 | g3642804 |
| HIV-1 child B193 J6195 isolate from Italy, envelope glycoprotein V3 region (env) gene, partial cds. | AF023315 | g3642806 |
| HIV-1 child B196 J4757 isolate from Italy, envelope glycoprotein V3 region (env) gene, partial cds. | AF023316 | g3642808 |
| HIV-1 child B196 J10001 isolate from Italy, envelope glycoprotein V3 region (env) gene, partial cds. | AF023317 | g3642810 |
| HIV-1 child B199 J4758 isolate from Italy, envelope glycoprotein V3 region (env) gene, partial cds. | AF023318 | g3642812 |
| HIV-1 child B199 J5513 isolate from Italy, envelope glycoprotein V3 region (env) gene, partial cds. | AF023319 | g3642821 |
| HIV-1 child B199 J27 isolate from Italy, envelope glycoprotein V3 region (env) gene, partial cds. | AF023320 | g3642823 |
| HIV-1 child B204 J4448 isolate from Italy, envelope glycoprotein V3 region (env) gene, partial cds. | AF023321 | g3642825 |
| HIV-1 child B204 J4755 isolate from Italy, envelope glycoprotein V3 region (env) gene, partial cds. | AF023322 | g3642829 |
| HIV-1 child B204 J5233 isolate from Italy, envelope glycoprotein V3 region (env) gene, partial cds. | AF023323 | g3642831 |
| HIV-1 child B204 J10003 isolate from Italy, envelope glycoprotein V3 region (env) gene, partial cds. | AF023324 | g3642833 |
| HIV-1 child B224 J5151 isolate from Italy, envelope glycoprotein V3 region (env) gene, partial cds. | AF023325 | g3642838 |
| HIV-1 child B224 J6363 isolate from Italy, envelope glycoprotein V3 region (env) gene, partial cds. | AF023326 | g3642840 |

-continued

| Chemokines GenBank Record | Accession No. | NID |
|---|---|---|
| HIV-1 child B224 J58 isolate from Italy, envelope glycoprotein V3 region (env) gene, partial cds. | AF023327 | g3642844 |
| HIV-1 child B224 J203 isolate from Italy, envelope glycoprotein V3 region (env) gene, partial cds. | AF023328 | g3642846 |
| HIV-1 child B32 J4070 isolate from Italy, envelope glycoprotein V3 region (env) gene, partial cds. | AF023329 | g3642848 |
| HIV-1 child B32 J5988 isolate from Italy, envelope glycoprotein V3 region (env) gene, partial cds. | AF023330 | g3642850 |
| HIV-1 child B32 J190 isolate from Italy, envelope glycoprotein V3 region (env) gene, partial cds. | AF023331 | g3642852 |
| HIV-1 child B3 J4443 isolate from Italy, envelope glycoprotein V3 region (env) gene, partial cds. | AF023332 | g3642860 |
| HIV-1 child B3 J6088 isolate from Italy, envelope glycoprotein V3 region (env) gene, partial cds. | AF023333 | g3642863 |
| HIV-1 child B3 J10005 isolate from Italy, envelope glycoprotein V3 region (env) gene, partial cds. | AF023334 | g3642865 |
| HIV-1 child B3 J62 isolate from Italy, envelope glycoprotein V3 region (env) gene, partial cds. | AF023335 | g3642868 |
| HIV-1 child B3 J176 isolate from Italy, envelope glycoprotein V3 region (env) gene, partial cds. | AF023336 | g3642870 |
| Gallid herpesvirus 1 CXC chemokine vIL8 mRNA, complete cds. | AF065430 | g3873222 |
| Human herpesvirus 6 serotype B putative major immediate-early genes. | U92288 | g2769711 |
| Human herpesvirus-6 (HHV-6) U1102, variant A, complete virion genome. | X83413 | g853961 |
| HIV-1 patient A isolate J2195 from Sweden, envelope glycoprotein V3 region (env) gene, partial cds. | U76078 | g1698913 |
| HIV-1 patient A isolate J4052 from Sweden envel. glycoprotein V3 region (env) gene, partial cds. | U76079 | g1698915 |
| HIV-1 patient B isolate J562 from Sweden, envelope glycoprotein V3 region (env) gene, partial cds. | U76080 | g1698917 |
| HIV-1 patient B isolate J975 from Sweden, envelope glycoprotein V3 region (env) gene, partial cds. | U76081 | g1698919 |
| HIV-1 patient C isolate J669 from Sweden, envelope glycoprotein V3 region (env) gene, partial cds. | U76082 | g1698921 |
| HIV-1 patient C isolate J1629 from Sweden, envelope glycoprotein V3 region (env) gene, partial cds. | U76083 | g1698923 |
| HIV-1 patient D isolate J1874 from Sweden, envelope glycoprotein V3 region (env) gene, partial cds. | U76084 | g1698925 |
| HIV-1 patient D isolate J2337 from Sweden, envelope glycoprotein V3 region (env) gene, partial cds. | U76085 | g1698927 |
| HIV-1 patient E isolate J2090 from Sweden, envelope glycoprotein V3 region (env) gene, partial cds. | U76086 | g1698929 |
| HIV-1 patient E isolate J2822 from Sweden, envelope glycoprotein V3 region (env) gene, partial cds. | U76087 | g1698931 |
| Kaposi's sarcoma-associated herpesvirus BCK gene, complete cds. | U83351 | g1778605 |
| qp81e03.x1 Soares_fetal_lung_NbHL19W *Homo sapiens* cDNA clone IMAGE:1929436 3' similar to TR:O15444 O15444 CHEMOKINE. :, mRNA sequence. | AI313153 | g4018758 |
| qx07c01.x1 NCI_CGAP_Lym12 *Homo sapiens* cDNA clone IMAGE:2000640 3' similar to TR:O00585 O00585 BETA CHEMOKINE EXODUS-2. :, mRNA sequence. | AI223954 | — |
| *Homo sapiens* CC chemokine LCC-1 precursor, gene, complete cds. | AF039954 | g4039073 |
| *Homo sapiens* liver CC chemokine-1 precursor (SCYA16) mRNA, complete cds. | AF039955 | g4039075 |
| Human C6 beta-chemokine mRNA, complete cds. | U67128 | g4097705 |
| Human chemokine alpha 3 (CKA-3) mRNA, complete cds. | U81234 | g4098960 |
| *Homo sapiens* CXC chemokine BRAK mRNA, complete cds. | AF073957 | g4140393 |
| Human monocyte chemotactic protein-4 precursor (MCP-4) mRNA, complete cds. | U59808 | g4097420 |
| *Homo sapiens* putative small inducible subfamily B-type cytokine (SCYB11) gene, partial cds. | AF053972 | g3746491 |

-continued

| Chemokines GenBank Record | Accession No. | NID |
|---|---|---|
| Human chemokine (hmrp-2a) mRNA, complete cds. | U58913 | g4204907 |
| Human chemokine (hmrp-2b) mRNA, complete cds. | U58914 | g4204909 |
| *Homo sapiens* gene for CC chemokine LEC, complete cds. | AB018249 | g4033626 |
| *Homo sapiens* gene encoding EBI1-ligand chemokine. | AJ223410 | g4128050 |
| *H. sapiens* mRNA for CC-chemokine. | Z77650 | g4128126 |
| *Homo sapiens* sic gene, exons 1 to 4. | AJ005654 | g4128128 |
| *H. sapiens* mRNA for CC-chemokine (sequence variant). | Z77651 | g4128134 |
| *Homo sapiens* mRNA for CC-chemokine MCP-4. | AJ001634 | g4138019 |
| *Homo sapiens* mRNA for chemokine IP-9. | Y15220 | g4225953 |
| functional macrophage inflammatory protein vmip-I homolog [Kaposi's sarcoma-associated herpesvirus] | U75698 | g1718266 |
| macrophage inflammatory protein vmip-ii homolog [Kaposi's sarcoma-associated herpesvirus] | U75698 | g1718264 |
| vmip-i, functional macrophage inflammatory protein 1-alpha homolog [Kaposi's sarcoma-associated herpesvirus] | U93872 | g2246546 |
| vmip-ii, macrophage inflammatory protein 1-alpha homolog [Kaposi's sarcoma-associated herpesvirus] | U93872 | g2246517 |
| vmip-1a [Kaposi's sarcoma-associated herpesvirus] | U74585 | g1658273 |
| vmip-1b [Kaposi's sarcoma-associated herpesvirus] | U67775 | g1562496 |

The peptides of the invention are optionally protected at the N-terminus and C-terminus with appropriate amino-terminal and/or carboxy terminal protecting groups, as described above. Where the peptide termini are unprotected, it is understood that the peptide N-terminus comprises an amino group (—NH$_2$) and that the peptide C-terminus comprises a carboxyl (—COOH) group.

The peptides of the invention may be recombinant peptides, natural peptides, or synthetic peptides. They may also be chemically synthesized, using, for example, solid phase synthesis methods.

In conventional solution phase peptide synthesis, the peptide chain can be prepared by a series of coupling reactions in which the constituent amino acids are added to the growing peptide chain in the desired sequence. The use of various N-protecting groups, e.g., the carbobenzyloxy group or the t-butyloxycarbonyl group, various coupling reagents (e.g., dicyclohexylcarbodiimide or carbonyidimidazole, various ctive esters, e.g., esters of N-hydroxyphthalimide or N-hydroxy-uccinimide, and the various cleavage reagents, e.g., trifluoroacetic acid TEA), HCI in dioxane, boron tris-(trifluoracetate) and cyanogen bromide, and reaction in solution with isolation and purification of intermediates is well-known classical peptide methodology. The preferred peptide synthesis method follows conventional Merrifield solid-phase procedures. See Merrifield, *J. Amer. Chem. Soc.* 85:2149–54 (1963) and *Science* 50:178–85 (1965). Additional information about the solid phase synthesis procedure can be had by reference to the treatise by Steward and Young (*Solid Phase Peptide Synthesis*, W. H. Freeman & Co., San Francisco, 1969, and the review chapter by Merrifield in *Advances in Enzymology* 32:221–296, F. F. Nold, Ed., Interscience Publishers, New York, 1969; and Erickson and Merrifield, *The Proteins* 2:255 et seq. (ea. Neurath and Hill), Academic Press, New York, 1976. The synthesis of peptides by solution methods is described in Neurath et al., eds. (*The Proteins*, Vol, II 3 d Ed., Academic Press, NY (1976)).

Crude peptides may be purified using preparative high performance liquid chromatography. The amino terminus may be blocked according, for example, to the methods described by Yang et al. (*FEBS Lett.* 272:61–64 (1990)).

Peptide synthesis includes both manual and automated techniques employing commercially available peptide synthesizers. The peptides of the invention may be prepared by chemical synthesis and biological activity can be tested using the methods disclosed herein.

The peptides of the invention may be synthesized in a manner such that one or more of the bonds linking amino acid residues are non-peptide bonds. These non-peptide bonds may be formed by chemical reactions well known to those skilled in the art. In yet another embodiment of the invention, peptides comprising the sequences described above may be synthesized with additional chemical groups present at their amino and/or carboxy termini, such that, for example, the stability, bio-availability, and/or inhibitory activity of the peptides is enhanced. For example, hydrophobic groups such as carbobenzoxyl, dansyl, or t-butyloxycarbonyl groups, may be added to the peptides' amino terminus. Likewise, an acetyl group or a 9-fluorenylmethoxy-carbonyl group may be placed at the peptides' amino terminus. Additionally, the hydrophobic group, t-butyloxycarbonyl, or an amido group, may be added to the peptides' carboxy terminus.

The peptides may be labeled, for further use as biomedical reagents or clinical diagnostic reagents. For example, a peptide of the invention can be conjugated with a fluorescent reagent, such as a fluorescein isothiocyanate (FITC), tetramethylrhodamine isothiocyanate (TRITC), or other fluorescent. The fluorescent reagent may be coupled to the peptide through the peptide N-terminus or free amine side chains by any one of the following chemistries, where R is the fluorescent reagent:

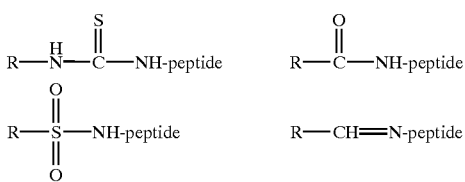

Alternatively, the peptide may be radiolabeled by peptide radiolabeling techniques well-known to those skilled in the art.

Further, the peptides of the invention may be synthesized such that their stearic configuration is altered. For example, the D-isomer of one or more of the amino acid residues of the peptide may be used, rather than the usual L-isomer. Still further, at least one of the amino acid residues of the peptide may be substituted by one of the well known non-naturally occurring amino acid residues. Alterations such as these may serve to increase the stability, bioavailability and/or inhibitory action of the peptides of the invention.

Alternatively, the peptides may be prepared utilizing recombinant DNA technology, which comprises combining a nucleic acid encoding the peptide thereof in a suitable vector, inserting the resulting vector into a suitable host cell, recovering the peptide produced by the resulting host cell, and purifying the polypeptide recovered. The techniques of recombinant DNA technology are known to those of ordinary skill in the art. General methods for the cloning and expression of recombinant molecules are described in Maniatis (*Molecular Cloning*, Cold Spring Harbor Laboratories, 1982), and in Sambrook (*Molecular Cloning*, Cold Spring Harbor Laboratories, Second Ed., 1989), and in Ausubel (*Current Protocols in Molecular Biology*, Wiley and Sons, 1987), which are incorporated by reference. The complete cDNA of human SDF-1 is reported, for example, under GenBank accession number U16752, incorporated herein by reference. From this nucleic acid sequence, synthetic genes encoding SDF-1-derived peptides may be synthesized directly on a DNA synthesizer, or may be synthesized as complementary oligonucleotides which are ligated together to form the synthetic gene. References to GenBank records for other chemokines are provided above.

The nucleic acids encoding the synthetic chemokine peptides may be operatively linked to one or more regulatory regions. Regulatory regions include promoters, polyadenylation signals, translation initiation signals (Kozak regions), termination codons, peptide cleavage sites, and enhancers. The regulatory sequences used must be functional within the cells of the vertebrate to be immunized. Selection of the appropriate regulatory region or regions is a routine matter, within the level of ordinary skill in the art.

Promoters that may be used in the present invention include both constitutive promoters and regulated (inducible) promoters. The promoters may be prokaryotic or eukaryotic depending on the host. Among the prokaryotic (including bacteriophage) promoters useful for practice of this invention are lac, lacZ, T3, T7, lambda Pr' Pl' and trp promoters. Among the eukaryotic (including viral) promoters useful for practice of this invention are ubiquitous promoters (e.g. HPRT, vimentin, actin, tubulin), intermediate filament promoters (e.g. desmin, neurofilaments, keratin, GFAP), therapeutic gene promoters (e.g. MDR type, CFTR, factor VI11), tissue-specific promoters (e.g. actin promoter in smooth muscle cells), promoters which respond to a stimulus (e.g. steroid hormone receptor, retinoic acid receptor), tetracycline-regulated transcriptional modulators, cytomegalovirus immediate-early, retroviral LTR, metallothionein, SV40, E1a, and MLP promoters. Tetracycline-regulated transcriptional modulators and CMV promoters are described in WO 96/01313, U.S. Pat. Nos. 5,168,062 and 5,385,839, the entire disclosures of which are incorporated herein by reference.

Examples of polyadenylation signals that can be used in the present invention include but are not limited to SV40 polyadenylation signals and LTR polyadenylation signals.

The peptides of the invention are prepared by either chemical synthesis or recombinant DNA technology may then be assayed for biological activity according to the assay methods described herein.

In some embodiments, the peptides of the present invention may be used in the form of a pharmaceutically acceptable salt.

Suitable acids which are capable of forming salts with the peptides include inorganic acids such as hydrochloric acid, hydrobromic acid, perchloric acid, nitric acid, thiocyanic acid, sulfuric acid, phosphoric acid and the like; and organic acids such as formic acid, acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid and the like.

Suitable bases capable of forming salts with the peptides include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanol-amines (e.g., ethanolamine, diethanolamine and the like).

The present invention provides methods for treating HIV-1 infection by inhibiting viral entry into cells expressing the CXCR4 receptor. Such CXCR4-expressing cells include, for example, T-cells. Accordingly, one or more SDF-1 peptides according to the invention is administered to a patient in need of such treatment. A therapeutically effective amount of the drug may be administered as a composition in combination with a pharmaceutically carrier.

Pharmaceutically acceptable carriers include physiologically tolerable or acceptable diluents, excipients, solvents, adjuvants, or vehicles, for parenteral injection, for intranasal or sublingual delivery, for oral administration, for rectal or topical administration or the like. The compositions are preferably sterile and nonpyrogenic. Examples of suitable carriers include but are not limited to water, saline, dextrose, mannitol, lactose, or other sugars, lecithin, albumin, sodium glutamate cysteine hydrochloride, ethanol, polyols (propyleneglycol, ethylene, polyethyleneglycol, glycerol, and the like), vegetable oils (such as olive oil), injectable organic esters such as ethyl oleate, ethoxylated isostearyl alcohols, polyoxyethylene sorbitol and sorbitan esters, microcrystalline cellulose, aluminum methahydroxide, bentonite, agar-agar and tragacanth, or mixtures of these substances, and the like.

The pharmaceutical compositions may also contain minor amounts of nontoxic auxiliary substances such as wetting agents, emulsifying agents, pH buffering agents, antibacterial and antifungal agents (such as parabens, chlorobutanol, phenol, sorbic acid, and the like). If desired, absorption enhancing or delaying agents (such as liposomes, aluminum monostearate, or gelatin) may be used. The compositions can be prepared in conventional forms, either as liquid solutions or suspensions, solid forms suitable for solution or suspension in liquid prior to injection, or as emulsions.

Compositions containing the SDF-1 peptides may be administered by any convenient route which will result in delivery to the site of infection of CXCR4-expressing cells by HIV-1, in an amount effective for inhibiting that infection from proceeding. Modes of administration include, for example, orally, rectally, parenterally (intravenously, intramuscularly, intraarterially, or subcutaneously), intracisternally, intravaginally, intraperitoneally, locally (powders, ointments or drops), or as a buccalor nasal spray or aerosol.

The pharmaceutical compositions are most effectively administered parenterally, preferably intravenously or subcutaneously. For intravenous administration, they may be dissolved in any appropriate intravenous delivery vehicle containing physiologically compatible substances, such as sodium chloride, glycine, and the like, having a buffered pH compatible with physiologic conditions. Such intravenous delivery vehicles are known to those skilled in the art. In a preferred embodiment, the vehicle is a sterile saline solution. If the peptides are sufficiently small, other preferred routes of administration are intranasal, sublingual, and the like. Intravenous or subcutaneous administration may comprise, for example, injection or infusion.

The SDF1-derived peptides according to the invention can be administered in any circumstance in which inhibition of HIV infection is desired. The peptides of the invention may be used for treatment of subjects as a preventative measure to avoid HIV infection, or as a therapeutic to treat patients already infected with HIV. The viruses whose transmission may be inhibited by the peptides of the invention include strains of HIV-1, but is most useful for those strains which gain entry via the CXCR4, such as T-tropic and dual-tropic strains. T-tropic strains utilize CXCR4 for entry, while dual-tropic strains utilize CXCR4 or CCR5 (Simmons et al., *J. Virol.* 70:8355–60, 1996). The peptides of the invention may be used prophylactically in uninfected individuals after exposed to an HIV virus. Examples of such uses include in the prevention of viral transmission from mother to infant, and following accidents in healthcare wherein workers may become exposed to HIV-contaminated blood, syringes and the like. The peptides may be administered to other individuals at risk of contracting HIV, such as homosexuals, prostitutes and intravenous drug users.

The SDF1-derived peptides may be administered alone or in combination with other peptides or other anti-HIV pharmaceutical agents. The effective amount and method of administration will vary based upon the sex, age, weight and disease stage of the patient, whether the administration is therapeutic or prophylactic, and other factors apparent to those skilled in the art. Based upon the studies described herein, a suitable dosage of peptide is a dosage which will attain a tissue concentration of from about 1 to about 100 $\mu$M, more preferably from about 10 to about 50 $\mu$M, most preferably about 25 $\mu$M. It is contemplated that lower or higher concentrations would also be effective. The tissue concentration may be derived from peptide blood levels.

The amount of active agent administered depends upon the degree of the infection. Those skilled in the art will derive appropriate dosages and schedules of administration to suit the specific circumstances and needs of the patient. Doses are contemplated on the order of from about 0.01 to about 1, preferably from about 0.1 to about 0.5, mg/kg of body weight. The active agent may be administered by injection daily, over a course of therapy lasting two to three weeks, for example. Alternatively, the agent may be administered by continuous infusion, such as via an implanted subcutaneous pumps.

EXAMPLES

A. Peptide Synthesis Procedure

The peptides of the invention, as well as other peptides prepared for comparison, were prepared synthetically as follows.

Peptides were prepared by solid phase peptide synthesis with Fmoc-strategy using a model 430A Applied Biosystems peptide synthesizer (Applied Biosystems, Foster City, Calif.) and Fmoc-tris (alkoxy) benzylamide liner (PAL-support) resin (Millipore, loading=0.38 mmole/g). The side chain-protecting groups of $N^\alpha$-Fmoc amino acids were: Arg; Pmc, Asn; Trt, Asp; O'Bu, Cys; Trt, Gln; Trt, Glu; O'Bu, His; Trt, Lys; Boc, Ser; ' Bu and Thr; ' Bu (Pmc=2,2,5,7, 8-pentamethylchroman-6-sulfonyl, Trt=Trityl, 'O Bu=tert-butyl ester, Boc=tert-butyloxycarbonyl and 'Bu=tert-butyl ether). NMethyl-2-pyrrolidinone (NMP) was used as a solvent and 20–50% piperidine in NMP was used to remove the protected Fmoc groups. Initially, the resin (660 mg, 0.25 mmole) was swollen with NMP and treated with piperidine to remove the Fmoc group. The $N^\alpha$-Fmoc amino acid (4 equiv.) activated with 2-(1H-Benzotriazole-1-yl) 1,1,3,3-tetra-methyluronium hexafluoro phosphate (HBTU) (4 equiv.) and diisopropylethylamine (DIPEA) (4 equiv.) was added to the resin for coupling followed by treatment with piperidine to remove the N-terminal Fmoc group. The coupling and deprotection steps were repeated for all the amino acid residues.

Upon completion of all synthetic cycles, resin was removed from the reaction vessel and treated with reagent K (King et al., Int. *J. Pep. Prot. Res.* 36:255–266, (1990) (Trifluoroacetic acid (TFA) :Phenol:thioanisole:ethandithiol:$H_2O$/10:0.75:0.5:0.25:0.5) for 1.5 hour at room temperature with gentle stirring. The mixture was then filtered directly into ice-cold methyl t-butyl ether. The resulting suspension was transferred into a centrifuge tube and centrifuged for 10 min. at 2000×g at room temperature. The supernatant was discarded and the precipitate was resuspended in methyl t-butyl ether, and again centrifuged for 5 minutes.

The procedure was repeated twice before the precipitate was dissolved in aqueous solvent and lyophilized.

The crude peptide was purified by preparative HPLC using Dynamax-300 Å C18 column (241×22 mm I.D., 15 mm spherical packing at a flow rate of 9 ml/min), with UV detection (220 nm). Two HPLC solvents, solvent A (d.i. $H_2O$/0.1% TFA) and B (Acetonitrile/0. 1% TFA) were used in a preprogrammed gradient. The fractions containing the peptide were pooled together and lyophilized.

The peptides were characterized by a procedure employing analytical HPLC, Mass Spectrometry and finally high resolution 600 MHz NMR spectroscopy. These procedures ensure that the final synthetic products are of >99% purity.

B. Peptides

The following peptides were synthesized according to the above procedure:

| Example No | SEQ ID NO: | Peptide |
|---|---|---|
| 1 | 4 | Leu-Ser-Tyr-Arg-Cys-Pro Cys-Arg-Phe-Phe-Gly-Gly-Gly-Gly-Leu-Lys-Trp-Ile-Gln-Glu-Tyr-Leu-Glu-Lys-Ala-Leu-Asn |
| 2 | 5 | Lys-Pro-Val-Ser-Leu-Ser-Tyr-Arg-Cys-Pro-Cys-Arg-Phe-Phe-Gly-Gly-Gln-Gly-Leu-Lys-Trp-Ile-Gln-Glu-Tyr-Leu-Glu-Lys-Ala-Leu-Asn |
| 3 | 6 | Leu-Ser-Tyr-Arg-Cys-Pro Cys-Arg-Phe-Phe-Gly-Gly-Leu-Lys-Trp-Ile-Gln-Glu-Tyr-Leu-Glu-Lys-Ala-Leu-Asn |

| Example No | SEQ ID NO: | Peptide |
|---|---|---|
| 4 | 7 | Leu-Ser-Tyr-Arg-Cys-Pro-Cys-Arg-Phe-Phe-Lys-Lys-Lys-Lys-Leu-Lys-Trp-Ile-Gln-Glu-Tyr-Leu-Glu-Lys-Ala-Leu-Asn |
| Comparative 1 | 8 | Leu-Ser-Tyr-Arg-Cys-Pro-Cys-Arg-Phe-Phe |
| Comparative 2 | 9 | Leu-Lys-Trp-Ile-Gln-Glu-Tyr-Leu-Glu-Lys-Ala-Leu-Asn |
| Comparative 3 | 10-CONH$_2$ | Lys-Pro-Val-Ser-Leu-Ser-Tyr-Arg-Cys-Pro-Cys-Arg-Phe-Phe-CONH$_2$ |

C. Biological Activity

A HIV-1 gp 120-CXCR4 mediated cell-cell fusion assay was used to test the effect of the above peptides on HIV-1 virus entry via CXCR4. The assay is based upon the cell-cell fusion assay described by Rucker et al., *Methods in Enzymology* 288:118–133 (1997) for studying the role of chemokine receptors in HIV-1 entry.

Effector and target cells were prepared as follows. HIV-1 Env proteins and T7 RNA polymerase were introduced into effector 293 cells by infection with recombinant vaccinia virus at a multiplicity of infection of 10 for 2 hours (the cell lines and HIV-1 isolates were kind gifts from R. W. Doms of University of Pennsylvania). QT6 target cells were transfected in 6-well plates with plasmids encoding CD4, CXCR4 and luciferase under control of the T7 promoter, using the calcium phosphate precipitation method. Four to six hours after transfection, cells were lifted, washed with PBS, seeded in 24-well plates and incubated at 37° C. overnight.

The effector and target cells were then subjected to fusion in the presence of SDF-1 peptide. To initiate fusion, $10^5$ effector cells were added to each well and incubated at 37° C. in the presence of ara-C, rifampicin and SDF-1 peptide (1 to 100 $\mu$M). After 5 hours of fusion, the cells were lysed in 150 $\mu$l of reporter lysis buffer (Promega) and assayed for luciferase activity by commercially available reagents (luciferase assay substrate, Promega Cat. No. E151A; luciferase assay buffer, Promega Cat. No. E152A). The results for peptides SEQ ID NOS:4–8 and 10, as percent inhibition of cell-cell fusion at a peptide concentration of 25 $\mu$M, are set forth in FIG. 1.

Each of the peptides SEQ ID NOS:4–7 contain segments from the N-terminal and C-terminal regions of SDF-1 linked through a homo-Gly or homo-Lys linker. Peptides SEQ ID NOS:4, 6 and 7 correspond to SDF-1 amino acids 5–14 and 55–67, linked by a bridge of (Gly)$_4$, (Gly)$_2$, and (Lys)$_4$, respectively. Peptide SEQ ID NO:5 corresponds to SDF-1 amino acids 1–14 and 55–67, linked by a (Gly)$_4$ bridge. The peptides of the invention (SEQ ID NOS:4, 5, 6 and 7) were substantially more effective in inhibiting cell-cell fusion than the N-terminal SDF-1 peptides SEQ ID NOS:8 and 10. The peptides of the invention were also more effective that the C-terminal SDF-1 peptide SEQ ID NO:9, which was only negligibly active at the higher concentration of 50 $\mu$M.

The peptides of the invention are more effective in preventing CXCR4-mediated entry of HIV-1 in CXCR4-expressing cells, and are more effective HIV therapeutic agents.

All references discussed herein are incorporated by reference. One skilled in the art will readily appreciate that the present invention is well adapted to carry out the objects and obtain the ends and advantages mentioned, as well as those inherent therein. The present invention may be embodied in other specific forms without departing from the spirit or essential attributes thereof and, accordingly, reference should be made to the appended claims, rather than to the foregoing specification, as indicating the scope of the invention.

What is claimed is:

1. A peptide which has the amino acid sequence Leu-Ser-Tyr-Arg-Cys-Pro-Cys-Arg-Phe-Phe-Gly-Gly-Gly-Gly-Leu-Trp-Ile-Gln-Tyr-Leu-Glu-Lys-Ala-Leu-Asn (SEQ ID NO:4) and optionally comprises an amino-terminal and/or carboxy-terminal protecting group.

2. A peptide which has the amino acid sequence Lys-Pro-Val-Ser-Leu-Ser-Tyr-Arg-Cys-Pro-Cys-Arg-Phe-Phe-Gly-Gly-Gly-Gly-Leu-Lys-Trp-Ile-Gln-Glu-Tyr-Leu-Glu-Lys-Ala-Leu-Asn (SEQ ID NO:5) and optionally comprises an amino-terminal and/or carboxy-terminal protecting group.

3. A peptide which has the amino acid sequence Leu-Ser-Tyr-Arg-Cys-Pro-Cys-Arg-Phe-Phe-Gly-Gly-Leu-Lys-Trp-Ile-Gln-Glu-Tyr-Leu-Glu-Lys-Ala-Leu-Asn (SEQ ID NO:6) and optionally comprises an amino-terminal and/or carboxy-terminal protecting group.

4. A peptide which has the amino acid sequence Leu-Ser-Tyr-Arg-Cys-Pro-Cys-Arg-Phe-Phe-Lys-Lys-Lys-Lys-Leu-Lys-Trp-Ile-Gln-Glu-Tyr-Leu-Glu-Lys-Ala-Leu-Asn (SEQ ID NO:7) and optionally comprises an amino-terminal and/or carboxy-terminal protecting group.

5. A pharmaceutical composition comprising a pharmaceutically acceptable carrier and the peptide of claim 1.

6. A pharmaceutical composition comprising a pharmaceutically acceptable carrier and the peptide of claim 2.

7. A pharmaceutical composition comprising a pharmaceutically acceptable carrier and the peptide of claim 3.

8. A pharmaceutical composition comprising a pharmaceutically acceptable carrier and the peptide of claim 4.

* * * * *

SEQUENCE LISTING

<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Segment
    from N-terminal region of human SDF-1 protein

<400> SEQUENCE: 1

Lys Pro Val Ser
 1

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Segment
    from N-terminal region of human SDF-1 protein

```
<400> SEQUENCE: 2

Glu Ser His Val Ala Arg Ala Asn
 1               5

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Segment
      from C-terminal region of human SDF-1 protein

<400> SEQUENCE: 3

Ile Asp Pro Lys
 1

<210> SEQ ID NO 4
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide containing segments from N- and C-terminal
      regions of human SDF-1 protein

<400> SEQUENCE: 4

Leu Ser Tyr Arg Cys Pro Cys Arg Phe Phe Gly Gly Gly Gly Leu Lys
 1               5                  10                  15

Trp Ile Gln Glu Tyr Leu Glu Lys Ala Leu Asn
             20                  25

<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide containing segments from N- and C-terminal
      regions of human SDF-1 protein

<400> SEQUENCE: 5

Lys Pro Val Ser Leu Ser Tyr Arg Cys Pro Cys Arg Phe Phe Gly Gly
 1               5                  10                  15

Gln Gly Leu Lys Trp Ile Gln Glu Tyr Leu Glu Lys Ala Leu Asn
             20                  25                  30

<210> SEQ ID NO 6
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide containing segments from N- and C-terminal
      regions of human SDF-1 protein

<400> SEQUENCE: 6

Leu Ser Tyr Arg Cys Pro Cys Arg Phe Phe Gly Gly Leu Lys Trp Ile
 1               5                  10                  15

Gln Glu Tyr Leu Glu Lys Ala Leu Asn
             20                  25

<210> SEQ ID NO 7
<211> LENGTH: 27
<212> TYPE: PRT
<213> ORGANISM: Artificial Sequence
```

```
<220> FEATURE:
<223> OTHER INFORMATION: Description of Artificial Sequence: Synthetic
      peptide containing segments from N- and C-terminal
      regions of human SDF-1 protein

<400> SEQUENCE: 7

Leu Ser Tyr Arg Cys Pro Cys Arg Phe Phe Lys Lys Lys Leu Lys
 1               5                  10                  15

Trp Ile Gln Glu Tyr Leu Glu Lys Ala Leu Asn
            20                  25

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide containing segment from N-terminal region
      of human SDF-1 protein

<400> SEQUENCE: 8

Leu Ser Tyr Arg Cys Pro Cys Arg Phe Phe
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide containing segment from C-terminal region
      of human SDF-1 protein

<400> SEQUENCE: 9

Leu Lys Trp Ile Gln Glu Tyr Leu Glu Lys Ala Leu Asn
 1               5                  10

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence:  Synthetic
      peptide containing segment from N-terminal region
      of human SDF-1 protein

<400> SEQUENCE: 10

Lys Pro Val Ser Leu Ser Tyr Arg Cys Pro Cys Arg Phe Phe
 1               5                  10

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Segment
      from N-terminal region of human SDF-1 protein

<400> SEQUENCE: 11

Leu Ser Tyr Arg
 1

<210> SEQ ID NO 12
<211> LENGTH: 10
<212> TYPE: PRT
```

-continued

```
<213> ORGANISM: Artificial Sequence
<220> FEATURE:
<223> OTHER INFORMATION: Description of Artificial Sequence: Segment
      from C-terminal region of human SDF-1 proteinein

<400> SEQUENCE: 12

Leu Lys Trp Ile Gln Glu Tyr Leu Glu Lys
  1               5                  10
```